United States Patent [19]

Berger et al.

[11] 4,244,652
[45] Jan. 13, 1981

[54] FERROELECTRIC LENGTH MEASURING AND MOVING TARGET TRANSDUCER WITH MEMORY

[75] Inventors: J. Louis Berger, Alexandria, Va.; L. Eric Cross, State College, Pa.

[73] Assignee: The United States of America as represented by the Secretary of the Army, Washington, D.C.

[21] Appl. No.: 958,071

[22] Filed: Nov. 6, 1978

[51] Int. Cl.³ .................... G01B 11/02; G01B 11/00
[52] U.S. Cl. ............................ 356/383; 250/211 R; 356/372; 356/373; 356/394
[58] Field of Search ............... 356/383, 372, 389, 373, 356/379, 394; 365/109, 117, 110; 350/363; 324/206; 250/560

[56] References Cited

U.S. PATENT DOCUMENTS

| | | | |
|---|---|---|---|
| 2,510,347 | 6/1950 | Perkins | 256/394 |
| 3,681,765 | 8/1972 | Chapman | 250/211 R |

FOREIGN PATENT DOCUMENTS 2002510  2/1979  United Kingdom ............... 356/373

OTHER PUBLICATIONS

Phillips, L. S., "A Ferroelectric Photoconductive Optical Information Store" Electronic components, 4-16-71, pp. 389–390.
Grenot et al., "New Electro-Optic Light Value Device for Image Storage & Processing", App. Phys. Lett., vol. 21, 1972, pp. 83–85

*Primary Examiner*—John K. Corbin
*Assistant Examiner*—Wm. H. Punter
*Attorney, Agent, or Firm*—Nathan Edelberg; Robert P. Gibson

[57] ABSTRACT

An electronic ferroelectric length measuring transducer and system for obtaining information and read-in of that information visually to determine the length of an image as well as means to determine if a target is moving. These actions are done very quickly and accurately by changing the polarization of a ferroelectric substrate. In addition, the information, once obtained, can be stored indefinitely without recourse to any external stimuli circuitry, until readout.

10 Claims, 7 Drawing Figures

FERROELECTRIC LENGTH MEASURING AND MOVING TARGET TRANSDUCER WITH MEMORY

DEDICATORY CLAUSE

The invention described herein may be manufactured, used, and licensed by or for the Government for governmental purposes without the payment to us of any royalties thereon.

BACKGROUND OF THE INVENTION

This invention relates to the field of measuring instruments.

There are numerous applications where it is necessary to ascertain the length of an object quickly and accurately by automated methods, or determine if a target is moving.

As an example of a length measuring application, there exist certain personnel identification devices used in physically secure installations where a person's identity is established by measuring his finger lengths.

Various personnel identification devices operate by use of movable photocells. However, these photocell devices use mechanical linkages which are cumbersome, subject to wear and relatively awkward to calibrate. There are other applications where rapidity of measurement is paramount, where the dimensions have to be accurately determined automatically. But as is well known, mechanical devices are relatively slow, compared to electronic devices, and subject to error. Thus, there is a need for a fast, accurate method to measure the length of objects.

As an additional application, the writing, storage and readout of moving targets constitute one of the more vital areas of research in the field of intrusion detection devices. Although the expertise necessary to construct a ferroelectric imaging device is well known, no attempt has been made to explore solutions for other imaging tasks more closely allied to the military or intrusion detection environment. Namely what is required is a simple, low power, moving target transducer. The fundamental problem in using the ferroelectric as a moving target transducer was in getting a readout of the information without recourse to steerable light beams or other relatively high power, relatively large devices.

Thus a need has been created for a simple, low power method of determining whether a target is moving.

Ferroelectrics have been used in the past as image transducers, but they have relied upon movement of the optical indicatrix of the ferroelectric with polarization, since polarization can be made a function of image intensity.

SUMMARY OF THE INVENTION

This invention makes direct use of the polarization properties of a ferroelectric, rather than the movement of the optical indicatrix for measuring the length of an object, or determining if a target is moving.

It is well understood that a square loop ceramic or crystalline ferroelectric, after originally being poled, has only two states of polarization: polarization with substantially all the domains oriented say, upwards or say, oriented downwards. When a ferroelectric is driven by, say, a positive going voltage pulse on the top surface, it can deliver a large charge into an integrating capacitor if the domains are previously oriented downwards or deliver a small charge if the domains were previously oriented upwards. The magnitude and direction of polarization then assumes the new value, and is effectively recorded, until again pulsed.

By utilization of a photoconductive coating plated onto the ferroelectric, the polarization can be made a function of whether or not there is an image present. What is done is to focus the image on the ferroelectric and operate a light source in conjunction with a voltage source. Either one source is pulsed and the other source kept steady or both sources can be pulsed. The ferroelectric must be prepoled each time an image presence is to be recorded.

In view of the above, it is a prime object of this invention to provide a completely electronic ferroelectric length measuring transducer and system for the obtaining and read-in of information visually, so as to determine the length of an image. It is another prime object of this invention to provide a means to determine if a target is moving.

The above stated actions are all done very quickly and accurately by means of changing the polarization of a ferroelectric substrate. No mechanically moving parts are required. The output of the transducer lends itself to automated use, being electrical.

It is an additional object of this invention to provide an image length measuring transducer or moving target transducer in which the information, upon being obtained, can be stored indefinitely without recourse to any external stimuli circuitry, until readout.

Various other objects and advantages will appear from the following description of the invention, and the most novel features will be particularly pointed out hereinafter in connection with the appended claims. It will be understood that various changes in the details, material and arrangement of the parts, which are herein described and illustrated in order to explain the nature of the invention may be made by those skilled in the art.

This invention may be better understood from the following detailed description taken in conjunction with the accompanying drawing.

DESCRIPTION OF THE PREFERRED EMBODIMENT

Figure 1:
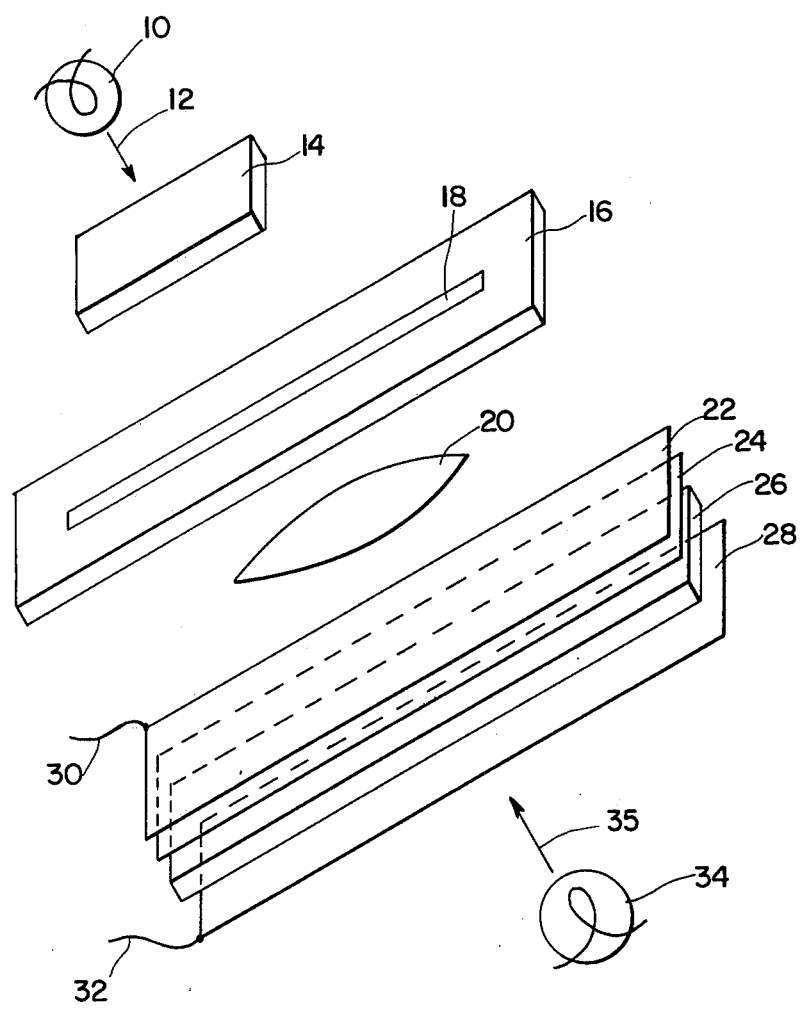
FIG. 1 is a diagrammatic and perspective view of the optical elements of the subject invention.

In accordance with the present invention in FIG. 1, is shown the light source 10, which may either be the ambient light or a lamp, and light energy 12 is caused to illuminate the object 14 whose length or movement is to be ascertained, whose image lies on an opaque plate 16 with one or more narrow width slots 18. Slots 18 are necessarily of a width narrower than the width of an object or finger whose length is being measured, and of a length longer than of that being measured. The light is collected and imaged by a lens 20 such that a real image appears on top of a transparent conductive coating 22 bonded to a photoconductive coating 24, which in turn is bonded onto the ferroelectric substrate 26, generally referred to hereinafter as the ferroelectric.

On the underside of the ferroelectric is placed a second transparent conductive coating 28. A wire 30 is connected to coating 22 and another wire 32 is connected to coating 28. Below the sandwich consisting of the transparent conductive coating 22, photoconductor 24, ferroelectric 26, and transparent conductive coating 28 is a second light source 34 and a second light energy 35. The light source 10 must be used during the write operation. The light source 34 is used during the poling and read operation. The light source 10 instead can be used to pole and read, provided the object 14 is removed from above the slot.

The method of operation depends first upon poling the ferroelectric; second, writing requires imaging the information from the object to be measured; and third, to read requires dumping out the charge, and reading it out on a high impedance voltmeter.

Figure 2A:
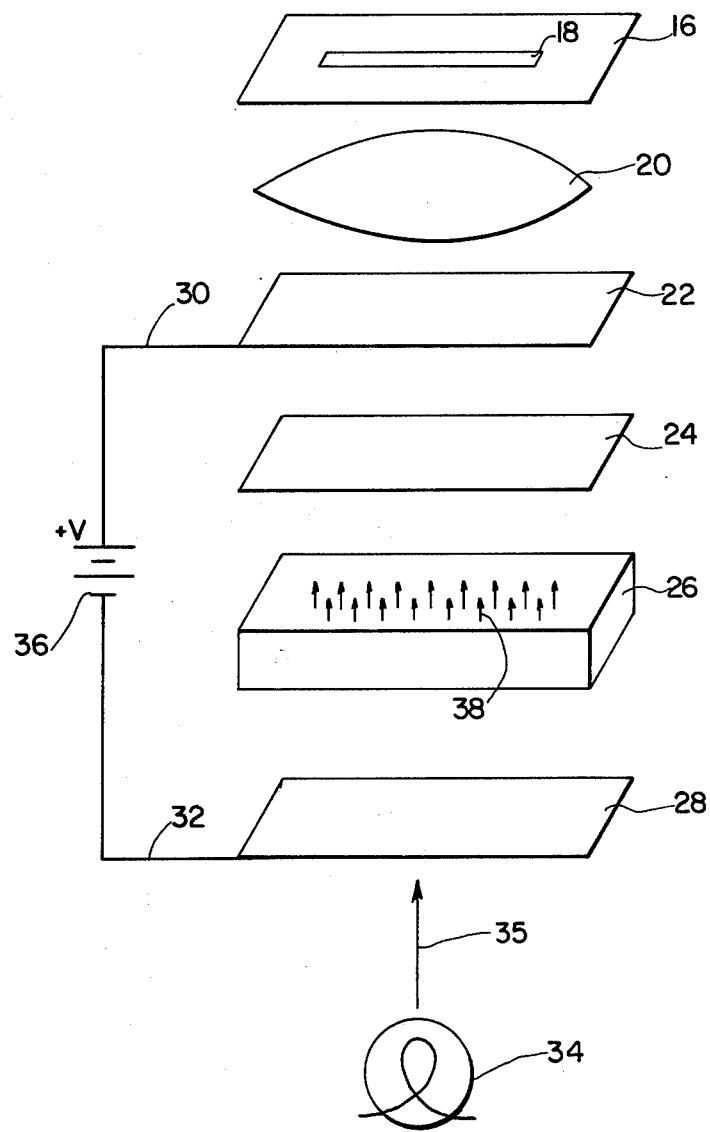
FIGS. 2A, 2B, and 2C illustrate schematically the electrical and optical elements of the subject invention in the poling, write and read modes, respectively when used as a length measuring transducer.
Figure 2B:
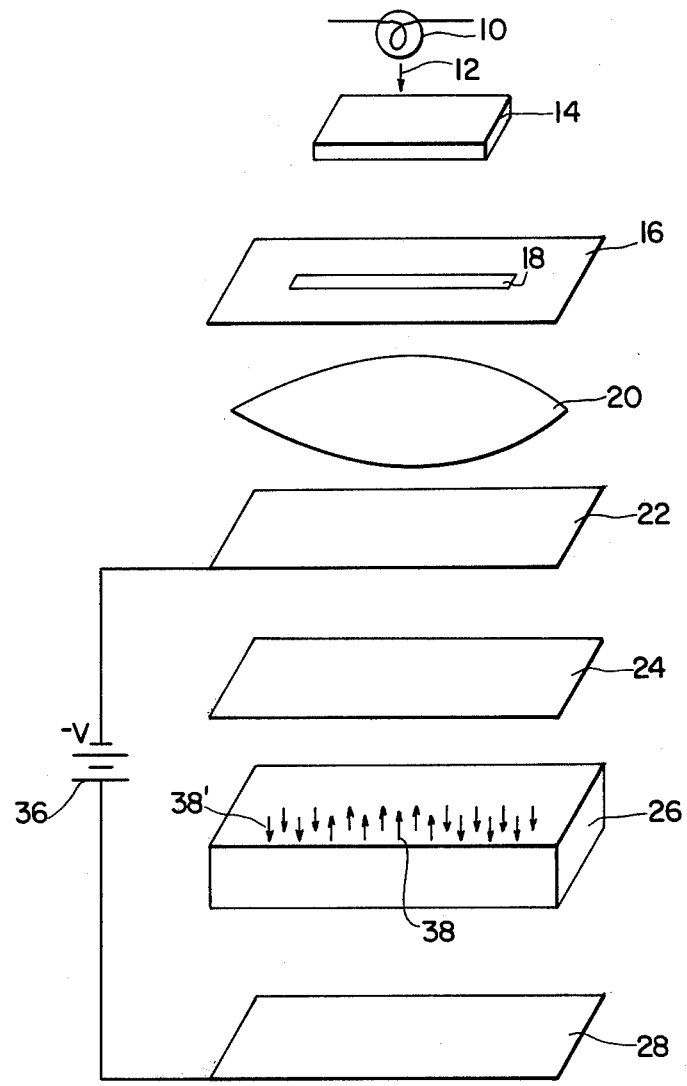
Figure 2C:
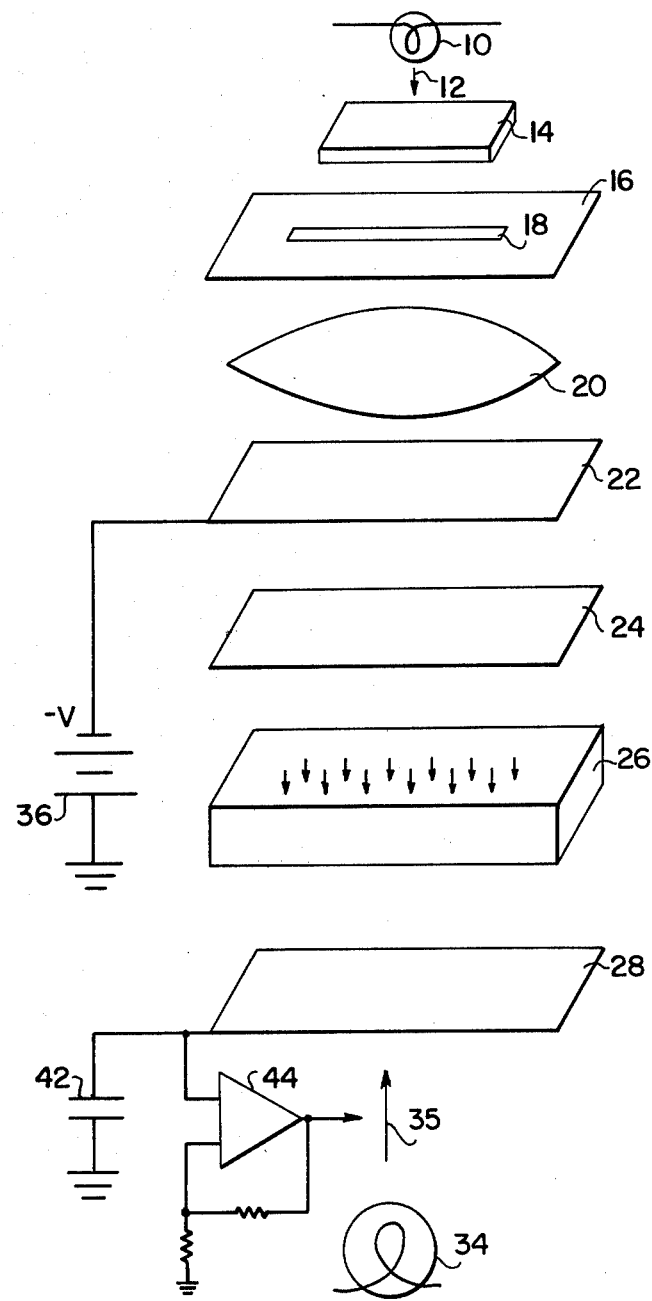

So as to obtain a further understanding, reference to FIGS. 2A, B, and C indicates how to use the invention as a length measuring device: poling the ferroelectric per FIG. 2A; writing in the length information per FIG. 2B; and reading the information out per FIG. 2C.

In FIG. 2A, with no image present, a potential $+V$, higher than the coercive field of the ferroelectric 26, is applied by battery 36 across the transparent conductive coating 22 and transparent conductive coating 28. The light source 34 is momentarily energized and light energy 35 goes through transparent conductive coating 28 and illuminates ferroelectric 26 and photoconductor 24.

The resistance of photoconductor 24, when illuminated, decreases over the surface of the ferroelectric 26. Therefore, essentially the entire battery potential is applied across the ferroelectric. The domains in the ferroelectric therefore orient themselves in an upwards direction, 38, in the volume directly under the slot 18 with an area equal to the cross-sectional area of the slot. The remainder of the ferroelectric does not reorient itself and is not used.

With the lamp then turned off, the high resistance of the photoconductor 24 will isolate the ferroelectric 26, which remains polarized in an upward direction indefinitely, until such time as a potential of opposite polarity is impressed, which can only be accomplished if the battery 36 is reversed and a light source momentarily turned on.

In FIG. 2B is shown the write operation. The battery 36 is reversed, with its negative terminal now on top, and transparent conductive coating 22 now negative. Transparent conductive coating 28 is now connected to the positive side of the battery. The object 14 to be imaged, whose width is greater than that of the slot 18 is placed on top of the slot. The light source 10 is momentarily turned on. Light energy 12 now illuminates the object 14 and goes through the narrow slot 18 in opaque table 16 onto lens 20.

An image is therefore cast onto the photoconductive coating. The portion of the photoconductor not illuminated represents a very high resistivity-on the order of $10^{12}$ ohm-centimeters. Therefore, the ferroelectric material under the high resistivity portion of the photoconductor will have only a small voltage across it, and the polarity of that portion of the ferroelectric will not change. The illuminated portion of the photoconductor represents a very low resistivity-on the order of $10^2$ ohm-centimeters, and the ferroelectric material under that portion of the photoconductor will reverse polarity as shown at 38. Therefore, what is left is a polarization picture of the image length to be measured with the domains still oriented upwards 38 where the image was cast and directed downwards 38, where there was complete illumination. This polarization picture will be stored indefinitely if the light is off or the voltage removed.

FIG. 2C depicts the read operation. Battery 36 is still connected with its negative terminal connected to transparent conductive coating 22 but the positive terminal is connected to ground. It is immaterial if the object 14 is present. A large capacitor, 42 is connected between the bottom transparent conductive coating 28 and ground. The capacitor will be used as an integrator to collect the charge on the ferroelectric. The lamp 34 is now turned on momentarily, directing light energy 35 upwards through the sandwich. The photoconductor 24 will now offer a low resistance across the surface of the ferroelectric. Accordingly, all the domains in the ferroelectric which were under the image will rotate downward. Rotating of these domains will cause a voltage to appear across capacitor 42 whose value is equal to $2Ps\ WL/C = KL$. where Ps is the saturation polarization of the ferroelectric which is a published value, W is the width of the slot 18, L is the length of the image, and C is the value of the integrating capacitor 42.

Therefore, a voltage has been generated equal to the image length and a proportionality constant K. This voltage can now be readout on a high impedance voltmeter 44. Note that since all the domains are now oriented downwards, the stored image length information has been destroyed, and if again required, will have to be re-imaged.

Figure 3A:
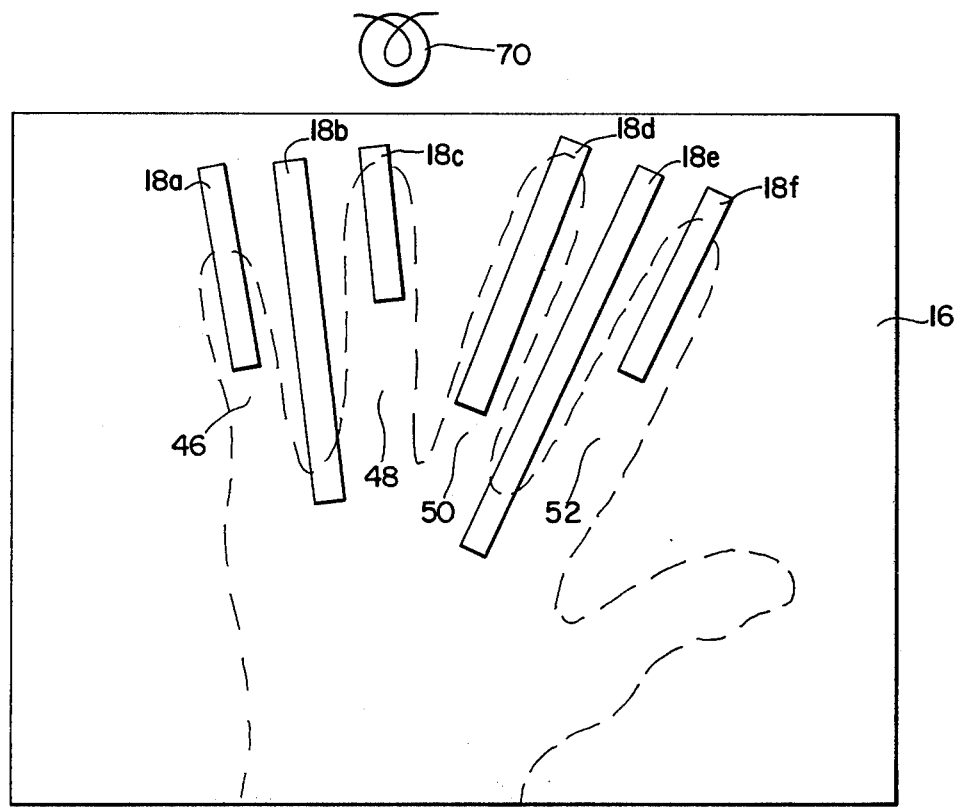
FIG. 3A is a view of a human hand over a multiple slotted part of the apparatus.
Figure 3B:
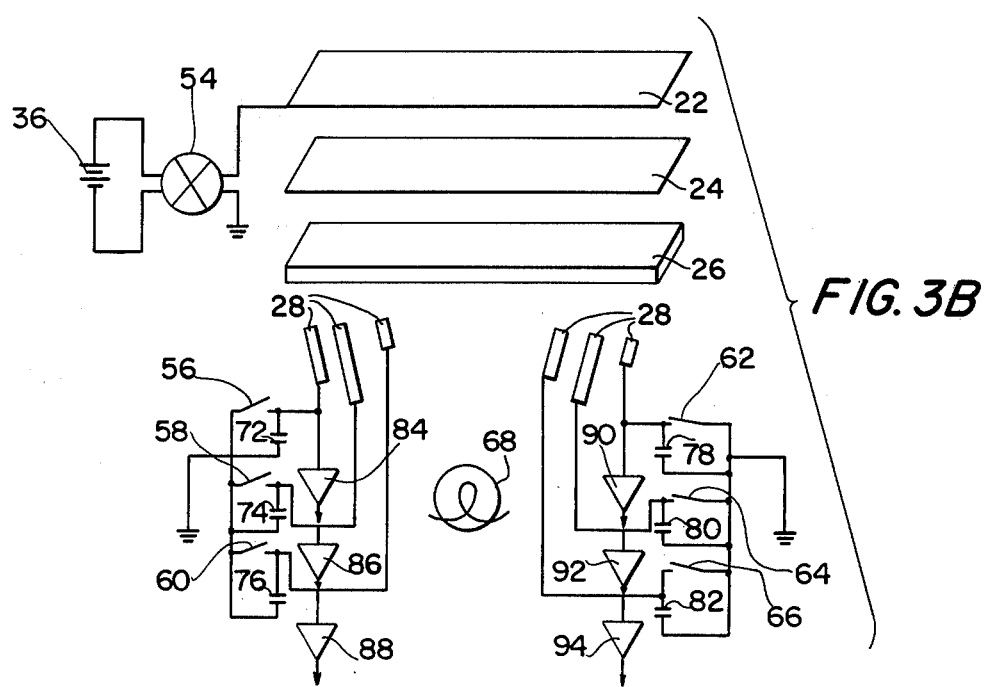
FIG. 3B is a generally perspective view of the sandwich and related schematic of the electronics necessary to readout the lengths of four fingers of the human hand.

As another particular example to demonstrate the practicality of this invention, consider its application as a finger length identifier for purposes of personnel identification. FIGS. 3A and 3B collectively depict the construction of the apparatus necessary to obtain the lengths of four fingers, excluding the thumb. When an opaque plate 16 with plurality of narrow slots 18 $a$–$f$ is used, the sandwich consists of a transparent conductive coating 22 coated onto a photoconductor 24, which was coated onto a transparent ferroelectric 26 and a plurality of transparent conductive segments 28, which were coated onto the bottom of the ferroelectric. The segments 28 are in registration with the slots. The six narrow slots 18$a$, 18$b$, 18$c$, 18$d$, 18$e$, and 18$f$ are so placed as to have the top edges of the first three slots at the same height. Similarly, the last three slots are at the same height. The four fingers 46, 48, 50, & 52, (shown in broken outline, FIG. 3) which are wider than the slots 18$a$, 18$c$, 18$d$, and 18$f$, are placed on the narrow slots and block out any light from getting through except for the portions of the slots beyond the fingers and hand.

To pole the ferroelectric, the positive end of battery 36 is connected through reversing switch 54 to the transparent conductive coating 22. The negative end of the battery is connected to ground. Switches 56, 58, 60, 62, 64, and 66 are closed, shorting the segments to ground. From below, a lamp 68 is momentarily energized. This causes all the domains in the ferroelectric directly between the top and bottom conductive coatings to be oriented upwards. The polarity of the remainder of the ferroelectric is of no concern as it will not vary, since only the portions of the ferroelectric between electrodes is subject to an electric field.

In the write process, the battery 36 is now reversed with its negative terminal now on top, using reversing switch 54. With the four fingers on the slots, a lamp 70 above the fingers is momentarily energized. All the domains between the conductive coatings that are exposed to the light energy now orient themselves in a downward direction.

In the read process, the switches 56, 58, 60, 62, 64, and 66 are opened and the six conductive segments are connected to the top end of their respective integrating capacitors, 72, 74, 76, 78, 80, and 82, with the bottom end of all the capacitors going to the positive battery terminal, and the negative battery terminal connected to the top transparent conductive coating 22. The lamp 68, below the transparent ferroelectric is momentarily energized. The charge from each capacitor is now read-out on high impedance voltmeters 84, 86, 88, 90, 92, and 94. The four finger lengths are now determined as being proportional to the difference reading between slots 18b and 18a, slots 18b and 18c, slots 18e and 18d, and slots 18e and 18f.

Figure 4:
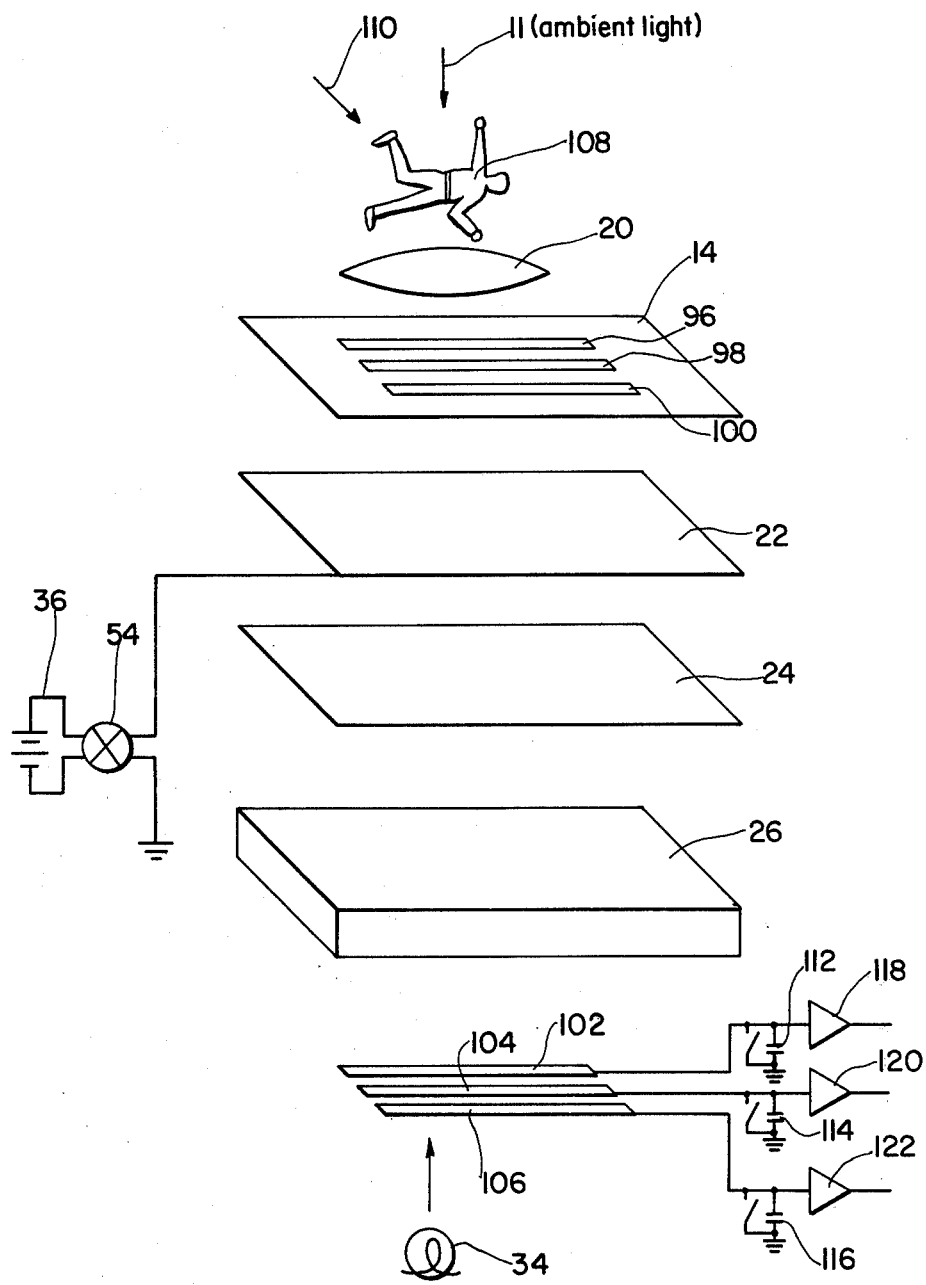
FIG. 4 is a perspective view of the sandwich and schematic of the electronics necessary to readout the presence of a moving target.

As another particular example of this invention's use, consider its application as a moving target indicator. FIG. 4 shows the typical construction of the sandwich necessary to determine if a target has moved: opaque plate 14 with slots 96, 98, and 100, transparent conductive coating 22, photoconductor 24, transparent ferroelectric 26 and transparent conductive segments 102, 104, and 106. The slots are in registration with the segments. Light source 34 is used to provide for the poling and read operation as heretofore. The write operation is dependent upon the ambient light 11 being of sufficient intensity to alter the resistance of the photoconductor as the object 108 moves in the direction 110. The lens 20 images the moving object onto the slots and the readout on the capacitors 112, 114, and 116 is accomplished as previously described. After each readout the ferroelectric must be again poled. The outputs from the voltmeters 118, 120, and 122 are monitored. If a significant change in a voltmeter reading is noted, it indicates a moving target. Of course, with more slots, a more comprehensive output is obtainable. The switch 54 and battery 36 perform the same functions as heretofore.

We claim:
1. Apparatus for measuring the length of an object having finite length and width dimensions, said apparatus comprising in combination:
   (1) a ferroelectric transducer having storage memory characteristics and having a high resistive impedance in the absence of light, which resistive impedance decreases responsive to incident light energy, said transducer including an assembly of
      (a) an elongated ferroelectric substrate having a longitudinal axis;
      (b) a photoconductive coating bonded to the upper side of said substrate;
      (c) first transparent conductive coating means bonded to the upper side of said photoconductive coating; and
      (d) second transparent conductive coating means bonded to the underside or lowerside of said substrate;
   (2) a d.c. voltage source;
   (3) means for electrically connecting said first and second transparent conductive coating means across said d.c. voltage source, said means including capacitive output impedence means;
   (4) means for deriving an output signal responsive to image-responsive voltage produced by said ferroelectric substrate across the capacitance impedance;
   (5) said ferroelectric substrate being inherently responsive to light energy from a related selected light source for producing light energy to activate said ferroelectric transducer;
   (6) means for focusing light energy from the selected light source upon a selected one of said transparent coatings;
   (7) a slotted opaque plate disposed between the selected transparent conductive coating means and the selected light source, said plate having at least one elongated narrow slot having a width less than the width of the object being measured and having a length greater than the object being measured,
   (8) said apparatus adapted to introduce a dimensionally defined object to be measured between the selected light source and at least one slot of said slotted opaque plate, and whereby the longitudinal axis of the elongated ferroelectric substrate is generally parallel to and in alignment with a corresponding longitudinal axis of the slot in said opaque plate.

2. The apparatus as defined in claim 1, wherein said selected light source is an electric lamp.

3. The apparatus as defined in claim 1, wherein the selected light source is incident to the first transparent conductive coating.

4. The apparatus as defined in claim 1, wherein the selected light source is incident to the second transparent conductive coating.

5. The apparatus as defined in claim 1, wherein said slotted opaque plate includes a plurality of narrow elongated slots disposed in generally parallel spaced apart relation.

6. The apparatus as defined in claim 1, wherein said slotted opaque plate includes a plurality of narrow elongated slots disposed in generally parallel but slightly converging but spaced apart relation.

7. The apparatus as defined in claim 1, further including means for changing the base level orientation of the ferroelectric substrate.

8. The apparatus as defined in claim 7, wherein said means for changing said base level orientation includes a second light source adapted to direct light energy through the other or non-selected one of said two transparent conductive coating means.

9. The apparatus as defined in claim 5, wherein said second transparent conductive coating means includes a plurality of separate transparent conductive coatings corresponding in number to the plurality of said slots, and said plurality of slots and transparent conductive coatings being disposed in spaced alignment with one another.

10. Apparatus as defined in claim 9 and adapted for also measuring the movement of an object across the opaque slotted plate thereof, the measuring of movement adapted to be made responsive to progressive movement of an object across said plurality of slots, and said apparatus including means responsive to the change in voltage between outputs obtained from the plurality of the separate transparent conductive coatings.

* * * * *